United States Patent [19]

Holyoke

[11] Patent Number: 4,502,880

[45] Date of Patent: Mar. 5, 1985

[54] 4-PYRIDINIUM QUINAZOLINE DERIVATIVES

[75] Inventor: Caleb W. Holyoke, Newark, Del.

[73] Assignee: E. I. Du Pont de Nemours and Company, Wilmington, Del.

[21] Appl. No.: 463,473

[22] Filed: Feb. 3, 1983

[51] Int. Cl.$^3$ .................... A01N 9/22; C07D 401/14
[52] U.S. Cl. ........................ 71/74; 544/283; 544/284; 71/92
[58] Field of Search ............... 544/284; 71/92, 74

[56] References Cited

U.S. PATENT DOCUMENTS

| | | | |
|---|---|---|---|
| 2,943,107 | 6/1960 | Rattenbury | 260/461 |
| 2,955,803 | 10/1960 | Goyette | 71/2.3 |
| 3,870,725 | 3/1975 | Hughes et al. | 544/284 |
| 4,026,906 | 5/1977 | Brewer et al. | 549/15 |
| 4,294,605 | 10/1981 | Arnet et al. | 71/73 |

FOREIGN PATENT DOCUMENTS

| | | | |
|---|---|---|---|
| 57-131771 | 8/1982 | Japan | 544/284 |
| 57-156467 | 9/1982 | Japan | 544/284 |
| 813531 | 4/1956 | United Kingdom . | |

*Primary Examiner*—Glennon H. Hollrah
*Assistant Examiner*—James H. Turnipseed

[57] ABSTRACT

Certain novel 2-chloro-4-pyridinium and 2,4-bis(-pyridinium)quinazolines are useful as cotton defoliants.

24 Claims, No Drawings

4-PYRIDINIUM QUINAZOLINE DERIVATIVES

BACKGROUND OF THE INVENTION

This invention relates to novel 2-chloro-4-pyridinium and 2,4-(bis)pyridinium quinazolines, to agricultural compositions containing them and to methods of using them as cotton defoliants.

The mature bolls of the cotton plant are typically mechanically harvested. The green leaves of the cotton plant can interfere with the harvest process as well as cause staining of the cotton fibers. To facilitate harvest and provide a higher quality crop, it is desirable to remove the leaves of the cotton plant prior to harvest. Removal of the leaves with chemicals is referred to as defoliation, and the chemicals causing this response are referred to defoliants.

Several defoliants are currently available commercially. These commercial products include the compounds tributyl phosphorotrithioite (Folex ®, Mobil Chemical Co.), S,S,S-tributylphosphorotrithioate (DEF, Mobay Chemical Corp.), N-phenyl-N'-1,2,3-thiadiazol-5-yl urea (Dropp ®, NOR-AM Agricultural Products, Inc.), and paraquat. The search continues, however, for products which are more effective defoliants, have better handling properties such as lack of odor and lower toxicity, are more effective in preventing regrowth of vegetation and are useful under a wider range of weather conditions.

SUMMARY OF THE INVENTION

It has now been found that the novel compounds of Formula I are useful as cotton defoliants. These compounds are advantageous in that they have no objectionable odor. It is also believed that they may be effective in preventing regrowth on treated plants.

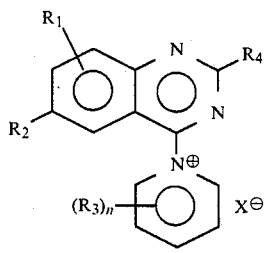

where
$R_1$ and $R_2$ are independently H, F, Cl, Br, or $C_1$-$C_4$ alkyl;
$R_3$ is $C_1$-$C_4$ alkyl;
$R_4$ is Cl or

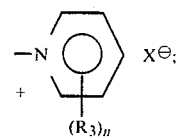

n is 0, 1, or 2; and
$X^\ominus$ is an agriculturally suitable anion; provided that when n is 1 or 2 and $R_3$ is in the 2- and/or 6-position of the pyridine ring, then $R_3$ is other than isopropyl, sec-butyl or tert-butyl.

This invention is therefore directed to the novel compounds of Formula I, agricultural compositions containing the compounds, and the method of using the compounds to defoliate cotton plants.

Compounds of Formula I where $R_1$ is H and $X^\ominus$ is $Cl^\ominus$ are preferred for their high activity and/or ease of synthesis.

Specifically preferred for the same reasons are the compounds:
1,1'-(2,4-quinazolinediyl)bis(pyridinium) dichloride, m.p. 159°–179° C. (dec.);
1,1'-(7-chloroquinazoline-2,4-diyl)bis(pyridinium) dichloride, m.p. 140° C. (dec.);
1-(2,6-dichloroquinazolin-4-yl)pyridinium chloride, m.p. 114°–120° C.; and
1-(2-chloroquinazolin-4-yl)pyridinium chloride, m.p. 105°–107° C.

DETAILED DESCRIPTION

Synthesis

The compounds of this invention can be prepared as shown in Equation 1.

EQUATION 1

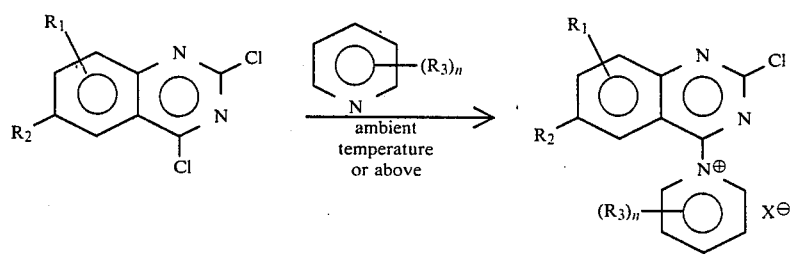

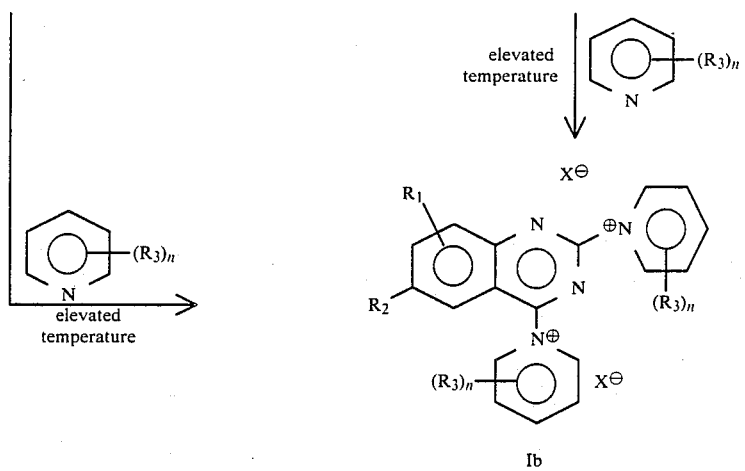

Compounds Ia (R$_4$=Cl) are prepared by contacting an appropriately substituted 2,4-dichloroquinazoline (II) with an excess of the appropriately substituted pyridine at ambient or moderately elevated temperature (e.g., about 20° to 120° C.), optionally in the presence of an inert solvent. Suitable solvents would include, for example, benzene and alkyl or halo-substituted benzenes. Compounds Ib (R$_4$=pyridinium) can be prepared in either of two ways. They may be prepared directly by contacting the appropriate 2,4-dichloroquinazoline with an excess of the appropriate pyridine at elevated temperatures (e.g., about 80°–200° C.). Alternatively, the 4-pyridinium-2-chloroquinazoline (Ia) is contacted with an excess of the appropriate pyridine at similarly elevated temperatures. Either process may be carried out in an inert solvent of appropriate boiling point or in an excess of the pyridine.

The procedure outlined above, utilizing a 2,4-dichloroquinazoline starting material leads to compounds of the invention where X$^\ominus$ is Cl$^\ominus$. Compounds where X$^\ominus$ is any other agriculturally suitable anion can be made by analogous methods or by exchanging Cl$^\ominus$ for other anions using methods well known in the art. Other examples of suitable anions include bromide and sulfate ions, and further examples would be known to one skilled in the art.

The 2,4-dichloroquinazolines (II) used as starting materials in these processes are described extensively in the art; for example by W. L. F. Armarego, *Quinazolines*, Part I of D. J. Brown (Ed.), *Fused Pyrimidines* (Volume 24 of *The Chemistry of Heterocyclic Compounds*, A. Weissberger (Ed.), Interscience (1967)). The pyridines are also well known; for example, see E. Klingsberg, *Pyridine and Its Derivatives Parts 1–4* (1960–64) and R. A. Abramovitch, *Pyridine and Its Derivatives*, supplement (1974). These references are to Volume 14 of *The Chemistry of Heterocyclic Compounds*, supra.

The preparation of compounds of this invention is illustrated by the following examples.

EXAMPLE 1

1-(2-Chloroquinazoline-4-yl)pyridinium chloride
(R$_1$=R$_2$=R$_3$=H; R$_4$=Cl, X$^\ominus$=Cl$^\ominus$)

A 50-g portion of 2,4-dichloroquinazoline was added to 500 ml of pyridine at ambient temperature. The reaction was stirred overnight under a calcium sulfate drying tube, chilled and filtered. The solid was rinsed thoroughly with pyridine and dried in vacuo giving 65 g of solid 1-(2-chloroquinazoline-4-yl)pyridinium chloride (m.p. 105°–107° C.; mixture melting point with 2,4-dichloroquinazoline 80°–87° C.).

(Note that these compounds are hygroscopic and the melting point varies widely on exposure to moist air.)

EXAMPLE 2

1,1'-(2,4-quinazolinediyl)bis(pyridinium) dichloride
(R$_1$=R$_2$=R$_3$=H; R$_4$=pyridinium; X$^\ominus$=Cl$^\ominus$)

Method A

A 20-g portion of 2,4-dichloroquinazoline was added to 200 ml of pyridine. The reaction mixture was stirred 1½ hours, refluxed 1½ hours, and then allowed to stir under a calcium sulfate drying tube for 3 days. The reaction mixture was filtered. The resulting solid rinsed well with pyridine, then ether, and was dried in vacuo giving 35.9 g of 1,1'-(2,4-quinazolinediyl)bis[pyridinium] dichloride (m.p. 150°–164°).

Method B

A 10-g portion of 1-(2-chloroquinazoline-4-yl)pyridinium chloride was added to 100 ml of pyridine under a calcium sulfate drying tube, refluxed 1½ hours, then allowed to stir 3 days. The reaction was filtered and the solid was rinsed with pyridine, then ether, and dried in vacuo giving 10.4 g of 1,1'-(2,4-quinazolinediyl)bis[pyridinium] dichloride (m.p. 156°–162° C.).

Using the procedures described above and illustrated in Examples 1–3, the compound listed in Tables I and II can be prepared.

TABLE I

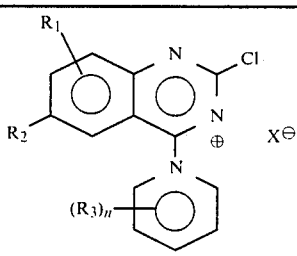

| R$_1$ | R$_2$ | R$_3$ | n | X | m.p. (°C.) |
|---|---|---|---|---|---|
| H | H | H | 0 | Cl | 105–107° |
| H | F | H | 0 | Cl | |

TABLE I-continued

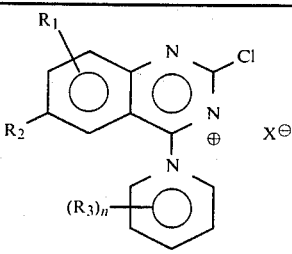

| R₁ | R₂ | R₃ | n | X | m.p. (°C.) |
|---|---|---|---|---|---|
| H | Cl | H | 0 | Cl | 114–120° |
| H | Br | H | 0 | Cl | |
| H | CH₃ | H | 0 | Cl | 122–125° |
| H | C₂H₅ | H | 0 | Cl | |
| H | n-C₃H₇ | H | 0 | Cl | |
| H | i-C₃H₇ | H | 0 | Cl | |
| 7-Cl | H | H | 0 | Cl | |
| 7-Cl | Cl | H | 0 | Cl | |
| 7-Cl | CH₃ | H | 0 | Cl | |
| H | H | 4-CH₃ | 1 | Cl | 228–230° |
| H | H | 3-CH₃ | 1 | Cl | |
| H | H | 2,4-CH₃ | 2 | Cl | 210° (dec) |
| H | Cl | 4-CH₃ | 1 | Cl | |
| H | Cl | 3-CH₃ | 1 | Cl | |
| H | Cl | 3,5-CH₃ | 2 | Cl | |
| H | H | H | 0 | Br | |
| H | Cl | H | 0 | Br | |
| H | CH₃ | H | 0 | Br | |
| 7-Cl | H | H | 0 | Cl | 98–100° |
| H | H | 2-CH₃ | 1 | Cl | 180° (dec) |
| H | H | 2,6-CH₃ | 2 | Cl | 226–235° |

TABLE II

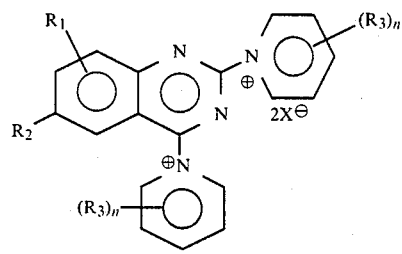

| R₁ | R₂ | R₃ | n | X | m.p. (°C.) |
|---|---|---|---|---|---|
| H | H | H | 0 | Cl | 159–170° |
| H | F | H | 0 | Cl | |
| H | Cl | H | 0 | Cl | 148° (dec) |
| H | Br | H | 0 | Cl | |
| H | CH₃ | H | 0 | Cl | 162–165° |
| H | C₂H₅ | H | 0 | Cl | |
| H | n-C₃H₇ | H | 0 | Cl | |
| H | i-C₃H₇ | H | 0 | Cl | |
| 7-Cl | H | H | 0 | Cl | |
| 7-Cl | Cl | H | 0 | Cl | |
| 7-Cl | CH₃ | H | 0 | Cl | |
| H | H | 4-CH₃ | 1 | Cl | |
| H | H | 3-CH₃ | 1 | Cl | |
| H | H | 2,4-CH₃ | 2 | Cl | >300° |
| H | Cl | 4-CH₃ | 1 | Cl | |
| H | Cl | 3-CH₃ | 1 | Cl | |
| H | Cl | 3,5-CH₃ | 2 | Cl | |
| H | H | H | 0 | Br | |
| H | Cl | H | 0 | Br | |
| H | CH₃ | H | 0 | Br | |
| 7-Cl | H | H | 0 | Cl | 140° (dec) |
| H | H | 2-CH₃ | 1 | Cl | |
| H | H | 2,6-CH₃ | 2 | Cl | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

| | Weight Percent | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 5–50 | 40–95 | 0–15 |
| Aqueous Suspension, Solution | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", Allured Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Ed., McGraw-Hill, New York, 1973, pp. 8–59ff.

For further information regarding the art of formulation, see for example:

H. M. Loux, U.S. Pat. No. 3,233,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

The following examples are illustrative of the formulations suitable for this invention.

EXAMPLE 3

Wettable Powder 1-(2-chloroquinazolin-4-yl)pyridinium chloride: 40%
dioctyl sodium sulfosuccinate: 1.5%
sodium ligninsulfonate: 3%
low viscosity methyl cellulose: 1.5%
attapulgite: 54%

The ingredients are thoroughly blended, passed through an air mill, to produce an average particle size under 15 microns, reblended, and sifted through a U.S.S. No. 50 sieve (0.3 mm opening) before packaging.

EXAMPLE 4

Wettable Powder 1-(2,6-dichloroquinazolin-4-yl)pyridinium chloride: 50%
sodium alkylnaphthalenesulfonate: 2%
low viscosity methyl cellulose: 2%
diatomaceous earth: 46%

The ingredients are blended, coarsely hammer-milled and then air-milled to produce particles essentially all below 10 microns in diameter. The product is reblended before packaging.

EXAMPLE 5

Wettable Powder 1,1'-(2,4-quinazolinediyl)bis(pyridinium) dichloride: 65%
dodecylphenol polyethylene glycol ether: 2%
sodium ligninsulfonate: 4%
sodium silicoaluminate: 6%
montmorillonite (calcined): 23%

The ingredients are thoroughly blended. The liquid surfactant is added by spraying upon the solid ingredients in the blender. After grinding in a hammer-mill to produce particles essentially all below 100 microns, the material is reblended and sifted through a U.S.S. No. 50 sieve (0.3 mm opening) and packaged.

EXAMPLE 6

Water Soluble Powder 1,1'-(7-chloroquinazoline-2,4-diyl)bis(pyridinium) dichloride: 95.0%
dioctyl sodium sulfosuccinate: 0.5%
sodium ligninsulfonate: 1.0%
synthetic fine silica: 3.5%

The ingredients are blended and coarsely ground in a hammer-mill so that only a few percent of the active exceeds 250 microns (U.S.S. No. 60 sieve) in size. When added to water with stirring, the coarse powder initially disperses and then the active ingredient dissolves so that no further stirring is needed during application.

EXAMPLE 7

Water Soluble Powder 1-(2,6-dichloroquinazolin-4-yl)pyridinium chloride: 95.0%
dioctyl sodium sulfosuccinate: 0.5%
sodium ligninsulfonate: 1.0%
synthetic fine silica: 3.5%

The ingredients are blended and coarsely ground in a hammer-mill so that only a few percent of the active exceeds 250 microns (U.S.S. No. 60 sieve) in size. When added to water with stirring, the coarse powder initially disperses and then the active ingredient dissolves so that no further stirring is needed during application.

EXAMPLE 8

Granule wettable powder of Example 3: 15%
gypsum: 69%
potassium sulfate: 16%

The ingredients are blended in a rotating mixer and water sprayed on to accomplish granulation. When most of the material has reached the desired range of 1.0 to 0.42 mm (U.S.S. No. 18 to 40 sieves), the granules are removed, dried, and screened. Oversize material is crushed to produce additional material in the desired range.

EXAMPLE 9

Granule 1-(2-chloroquinazolin-4-yl)pyridinium chloride: 10%
water: 20%
preformed diatonite granule: 70%

The active ingredient is dissolved in warm water and sprayed onto a tumbling bed of the preformed granules. The finished granular product is packaged immediately to prevent any loss of water.

Utility

Test results indicate that the compounds of this invention are useful as cotton defoliants. They may be applied post-emergence to cotton plants. The precise amount of the compound to be used in a given situation will vary according to the degree of plant maturity, the variety of cotton planted, the weather conditions, the formulations, the method of application, etc. Since so many variables play a role, it is not possible to state a rate of application for all situations. Broadly speaking, the compounds of this invention are used at levels of 0.01 to 10 kg/ha with a preferred range of 0.1 to 2 kg/ha. The compounds would be applied post-emergence to the foliage of cotton plants which are approaching maturity. Maturity here refers to the ripening (opening) of the bolls of the cotton plant. Application can be made by aircraft or by a suitable agricultural sprayer.

The utility of the compounds of this invention was discovered in greenhouse tests performed as follows.

TEST PROCEDURE

Seeds of cotton (*Gossypium hirsutum* var. Stoneville 213) were planted in Woodstown sandy loam soil or a commercial growth medium such as Metro-Mix ® 200. As cotton plants approached maturity, approximately four months later, the leaves were counted and marked. Experimental compounds were dissolved in a non-phytotoxic solvent and applied as an overall spray to the foliage. At one and three week intervals, the marked leaves remaining on the plant were counted. The number of leaves which had defoliated was determined and the degree of defoliation expressed as a percentage. When more than one plant was sprayed, the average was calculated. The percent defoliation for untreated checks at three weeks was also calculated. The results are tabulated in Table III.

Compounds Tested -continued

Compound 11

![Compound 11 structure: quinazoline with Cl and N-methylpyridinium, Cl⁻ counterion]

Compound 12

![Compound 12 structure: quinazoline with Cl and N-(2-methylpyridinium), Cl⁻ counterion]

Compound 13

![Compound 13 structure: quinazoline with Cl and N-(2,6-dimethylpyridinium), Cl⁻ counterion]

TABLE III

| | | Application Rate (g/ha) | Percent Defoliation[1] 1 Week Rating | 3 Week Rating |
|---|---|---|---|---|
| Compound 1 | Test 1 | 250 | 52 | 98 |
| | | 1000 | 90 | 96 |
| | Check | — | — | 4 |
| | Test 2 | 62 | 51 | 76 |
| | | 250 | 84 | 93 |
| | | 1000 | 88 | 97 |
| | Check | — | — | 30 |
| | Test 3 | 63 | 9 | 24 |
| | | 250 | 22 | 45 |
| | Check | — | — | 29 |
| | Test 4 | 63 | 18 | 28 |
| | | 250 | 23 | 40 |
| | | 1000 | 52 | 64 |
| | Check | — | — | 15 |
| Compound 2 | | 62 | 6 | 28 |
| | | 250 | 22 | 43 |
| | Check | — | — | 29 |
| Compound 3 | Test 1 | 62 | 5 | 43 |
| | | 250 | 2 | 22 |
| | Check | — | — | 29 |
| | Test 2 | 250 | 0 | 6 |
| | Check | — | — | 15 |
| Compound 4 | | 62 | 2 | 11 |
| | | 250 | 10 | 33 |
| | Check | — | — | 29 |
| Compound 5 | Test 1 | 62 | 15 | 34 |
| | | 250 | 64 | 83 |
| | Check | — | — | 29 |
| | Test 2 | 250 | 85 | 100 |
| | | 1000 | 73 | 96 |
| | Check | — | — | 15 |
| Compound 6 | | 62 | 10 | 14 |
| | | 250 | 2 | 24 |
| | Check | — | — | 29 |
| Compound 7 | | 62 | 5 | 7 |
| | | 250 | 8 | 27 |
| | Check | — | — | 29 |
| Compound 8 | | 62 | 10 | 19 |

TABLE III-continued

| | | Application Rate (g/ha) | Percent Defoliation[1] 1 Week Rating | 3 Week Rating |
|---|---|---|---|---|
| | | 250 | 13 | 32 |
| | Check | — | — | 29 |
| Compound 9 | | 62 | 8 | 19 |
| | | 250 | 4 | 23 |
| | Check | — | — | 29 |
| Compound 10 | Test 1 | 62 | 31 | 62 |
| | | 250 | 89 | 93 |
| | | 1000 | 94 | 99 |
| | Check | — | — | 30 |
| | Test 2 | 62 | 2 | 12 |
| | | 250 | 10 | 32 |
| | Check | — | — | 29 |
| | Test 3 | 250 | 20 | 28 |
| | Check | — | — | 15 |
| Compound 11 | Test 1 | 62 | 26 | 43 |
| | | 250 | 14 | 41 |
| | | 1000 | 12 | 25 |
| | Check | — | — | 30 |
| Compound 12 | | 62 | 3 | 14 |
| | | 250 | 3 | 23 |
| | Check | — | — | 29 |
| Compound 13 | | 62 | 6 | 16 |
| | | 250 | 6 | 30 |
| | Check | — | — | 29 |

[1] Percent Defoliation = $100 \times \left[1 - \dfrac{\text{number of leaves remaining}}{\text{number of leaves present initially}}\right]$ The results in Table III indicate that the compounds of this invention are useful as cotton defoliants. It is believed that the few compounds which did not show a percent defoliation greater than that of the untreated check would be active at higher rates of application.

What is claimed is:

1. A compound of the formula:

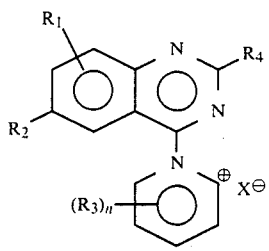

where
$R_1$ and $R_2$ are independently H, F, Cl, Br, or $C_1$–$C_4$ alkyl;
$R_3$ is $C_1$–$C_4$ alkyl;
$R_4$ is Cl or

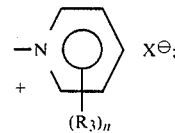

$n$ is 0, 1 or 2; and
$X^\ominus$ is an agriculturally suitable anion; provided that when $n$ is 1 or 2 and $R_3$ is in the 2- and/or 6-position of the pyridine ring, then $R_3$ is other than isopropyl, sec-butyl or tert-butyl.

2. A compound of claim 1 where $R_1$ is H.
3. A compound of claim 1 where $X^\ominus$ is $Cl^\ominus$.
4. A compound of claim 2 where $X^\ominus$ is $Cl^\ominus$.

5. The compound of claim 1 which is 1,1'-(2,4-quinazolinediyl)bis(pyridinium) dichloride.

6. The compound of claim 1 which is 1,1'-(7-chloroquinazoline-2,4-diyl)bis(pyridinium) dichloride.

7. The compound of claim 1 which is 1-(2,6-dichloroquinazolin-4-yl)pyridinium chloride.

8. The compound of claim 1 which is 1-(2-chloroquinazolin-4-yl)pyridinium chloride.

9. An agricultural composition comprising an effective defoliant amount of a compound of claim 1 and at least one of (a) a surfactant and (b) a solid or liquid diluent.

10. An agricultural composition comprising an effective defoliant amount of a compound of claim 2 and at least one of (a) a surfactant and (b) a solid or liquid diluent.

11. An agricultural composition comprising an effective defoliant amount of a compound of claim 3 and at least one of (a) a surfactant and (b) a solid or liquid diluent.

12. An agricultural composition comprising an effective defoliant amount of a compound of claim 4 and at least one of (a) a surfactant and (b) a solid or liquid diluent.

13. An agricultural composition comprising an effective defoliant amount of a compound of claim 5 and at least one of (a) a surfactant and (b) a solid or liquid diluent.

14. An agricultural composition comprising an effective defoliant amount of a compound of claim 6 and at least one of (a) a surfactant and (b) a solid or liquid diluent.

15. An agricultural composition comprising an effective defoliant amount of a compound of claim 7 and at least one of (a) a surfactant and (b) a solid or liquid diluent.

16. An agricultural composition comprising an effective defoliant amount of a compound of claim 8 and at least one of (a) a surfactant and (b) a solid or liquid diluent.

17. A method for defoliating cotton plants comprising applying to the foliage of said plants an effective defoliant amount of a compound of claim 1.

18. A method for defoliating cotton plants comprising applying to the foliage of said plants an effective defoliant amount of a compound of claim 2.

19. A method for defoliating cotton plants comprising applying to the foliage of said plants an effective defoliant amount of a compound of claim 3.

20. A method for defoliating cotton plants comprising applying to the foliage of said plants an effective defoliant amount of a compound of claim 4.

21. A method for defoliating cotton plants comprising applying to the foliage of said plants an effective defoliant amount of a compound of claim 5.

22. A method for defoliating cotton plants comprising applying to the foliage of said plants an effective defoliant amount of a compound of claim 6.

23. A method for defoliating cotton plants comprising applying to the foliage of said plants an effective defoliant amount of a compound of claim 7.

24. A method for defoliating cotton plants comprising applying to the foliage of said plants an effective defoliant amount of a compound of claim 8.

* * * * *